US011033450B2

(12) United States Patent
Lamb et al.

(10) Patent No.: US 11,033,450 B2
(45) Date of Patent: Jun. 15, 2021

(54) LEG EXOSKELETON SYSTEM AND METHOD

(71) Applicant: Roam Robotics Inc., San Francisco, CA (US)

(72) Inventors: Callum Russell Lamb, San Bruno, CA (US); Giancarlo Sigurd Sante Nucci, Seattle, WA (US); Kyle Allen Lamson, San Francisco, CA (US); Timothy Alan Swift, Albany, CA (US); Brenton Piercy, San Francisco, CA (US); Peter Sturt Lynn, Oakland, CA (US)

(73) Assignee: ROAM ROBOTICS INC., San Francisco, CA (US)

( * ) Notice: Subject to any disclaimer, the term of this patent is extended or adjusted under 35 U.S.C. 154(b) by 219 days.

(21) Appl. No.: 15/953,296

(22) Filed: Apr. 13, 2018

(65) Prior Publication Data

US 2018/0296425 A1 Oct. 18, 2018

Related U.S. Application Data

(60) Provisional application No. 62/485,279, filed on Apr. 13, 2017.

(51) Int. Cl.
*A61F 5/01* (2006.01)
*A61H 3/00* (2006.01)
(Continued)

(52) U.S. Cl.
CPC ............. *A61H 3/00* (2013.01); *A61F 5/0125* (2013.01); *A61H 1/024* (2013.01); *A63C 11/16* (2013.01);
(Continued)

(58) Field of Classification Search
CPC ........................... A61F 2002/747; F16J 3/048
(Continued)

(56) References Cited

U.S. PATENT DOCUMENTS 440,684 A 11/1890 Yagn
3,823,711 A 7/1974 Hatton
(Continued)

FOREIGN PATENT DOCUMENTS

EP 3173191 A2 5/2017
WO 9722782 A1 6/1997
(Continued)

OTHER PUBLICATIONS

U.S. Appl. No. 13/662,308, filed Oct. 26, 2012.
(Continued)

*Primary Examiner* — David H Willse
(74) *Attorney, Agent, or Firm* — Davis Wright Tremaine

(57) ABSTRACT

A fluidic exoskeleton system. The system can include one or more fluidic actuator units that have: a joint; a first and second arm coupled to the joint; an inflatable bellows actuator extending between a first and second plate associated with the joint, the inflatable bellows actuator defining a bellows cavity, the inflatable bellows actuator configured to extend along a length of the bellows actuator when inflated by introducing fluid into the bellows cavity; and one or more constraint ribs extending from the joint and surrounding portions of the bellows actuator along the length of the bellows actuator.

16 Claims, 12 Drawing Sheets

(51) Int. Cl.
  *F16J 3/04* (2006.01)
  *A63C 11/16* (2006.01)
  *A61H 1/02* (2006.01)
  *B25J 9/00* (2006.01)
  *A61F 2/74* (2006.01)

(52) U.S. Cl.
  CPC ............ B25J 9/0006 (2013.01); F16J 3/048 (2013.01); *A61F 2002/747* (2013.01); *A61F 2005/0155* (2013.01); *A61H 2003/001* (2013.01); *A61H 2003/007* (2013.01); *A61H 2201/0103* (2013.01); *A61H 2201/1207* (2013.01); *A61H 2201/1238* (2013.01); *A61H 2201/1261* (2013.01); *A61H 2201/165* (2013.01); *A61H 2201/1642* (2013.01); *A61H 2201/1671* (2013.01); *A61H 2201/5007* (2013.01); *A61H 2201/5012* (2013.01); *A61H 2201/5061* (2013.01); *A61H 2201/5064* (2013.01); *A61H 2201/5084* (2013.01); *A63C 2203/50* (2013.01)

(58) Field of Classification Search
  USPC .................................................. 92/42
  See application file for complete search history.

(56) References Cited

U.S. PATENT DOCUMENTS

| | | | |
|---|---|---|---|
| 3,868,952 | A | 3/1975 | Hatton |
| 3,982,531 | A | 9/1976 | Shaffer |
| 3,993,056 | A | 11/1976 | Rabischong et al. |
| 4,274,399 | A | 6/1981 | Mummert |
| 4,523,582 | A | 6/1985 | Barber |
| 4,671,258 | A | 6/1987 | Barthlome |
| 4,944,755 | A | 7/1990 | Hennequin et al. |
| 5,033,457 | A | 7/1991 | Bonutti |
| 5,483,838 | A | 1/1996 | Holden |
| 7,086,322 | B2 * | 8/2006 | Schulz ................. F15B 15/103 92/42 |
| 7,479,121 | B2 | 1/2009 | Branch |
| 8,171,570 | B2 | 5/2012 | Adarraga |
| 8,784,350 | B2 | 7/2014 | Cohen |
| 9,205,560 | B1 | 12/2015 | Edsinger et al. |
| 9,821,475 | B1 | 11/2017 | Lynn et al. |
| 9,995,321 | B2 | 6/2018 | Lynn et al. |
| 10,012,229 | B2 | 7/2018 | Lynn et al. |
| 10,562,180 | B2 | 2/2020 | Telleria et al. |
| 10,605,365 | B1 | 3/2020 | Griffith et al. |
| 10,619,633 | B2 | 4/2020 | Lynn et al. |
| 2001/0029343 | A1 | 10/2001 | Seto et al. |
| 2002/0026794 | A1 | 3/2002 | Shahinpoor et al. |
| 2006/0069336 | A1 | 3/2006 | Krebs et al. |
| 2006/0161220 | A1 | 7/2006 | Kobayashi et al. |
| 2008/0009771 | A1 | 1/2008 | Perry et al. |
| 2008/0195005 | A1 | 8/2008 | Horst et al. |
| 2008/0287850 | A1 | 11/2008 | Adarraga |
| 2010/0204627 | A1 | 8/2010 | Kazerooni et al. |
| 2010/0249675 | A1 | 9/2010 | Fujimoto et al. |
| 2010/0280424 | A1 | 11/2010 | Kawakami et al. |
| 2011/0071417 | A1 | 3/2011 | Liu et al. |
| 2011/0118635 | A1 | 5/2011 | Yamamoto |
| 2012/0289870 | A1 | 11/2012 | Hsiao-Wecksler et al. |
| 2013/0150980 | A1 | 6/2013 | Swift et al. |
| 2013/0158445 | A1 | 6/2013 | Kazerooni et al. |
| 2013/0245512 | A1 | 9/2013 | Goffer et al. |
| 2013/0289452 | A1 | 10/2013 | Smith et al. |
| 2014/0109560 | A1 | 4/2014 | Ilievski et al. |
| 2014/0276264 | A1 | 9/2014 | Caires et al. |
| 2014/0277739 | A1 | 9/2014 | Kornbluh et al. |
| 2014/0318118 | A1 | 10/2014 | Mazzeo et al. |
| 2015/0088043 | A1 | 3/2015 | Goldfield et al. |
| 2015/0173993 | A1 | 6/2015 | Walsh et al. |
| 2015/0209214 | A1 | 7/2015 | Herr et al. |
| 2015/0290794 | A1 | 10/2015 | Griffith et al. |
| 2016/0107309 | A1 | 4/2016 | Walsh et al. |
| 2016/0213548 | A1 | 7/2016 | John et al. |
| 2016/0261224 | A1 | 9/2016 | Madrone et al. |
| 2016/0278948 | A1 | 9/2016 | Piercy et al. |
| 2016/0297504 | A1 * | 10/2016 | Saindon ................. F16J 3/048 |
| 2016/0331557 | A1 | 11/2016 | Tong et al. |
| 2017/0049587 | A1 | 2/2017 | Herr et al. |
| 2018/0125152 | A1 * | 5/2018 | Bruel ...................... A43B 7/16 |
| 2018/0235830 | A1 | 8/2018 | Rokosz et al. |
| 2018/0283414 | A1 | 10/2018 | Lynn et al. |
| 2019/0015233 | A1 | 1/2019 | Galloway et al. |
| 2019/0060156 | A1 | 2/2019 | Swift et al. |
| 2019/0307583 | A1 | 10/2019 | Herr et al. |

FOREIGN PATENT DOCUMENTS

| | | | |
|---|---|---|---|
| WO | 0004852 A1 | 2/2000 | |
| WO | 2015080596 A1 | 6/2015 | |
| WO | 2016166588 A1 | 10/2016 | |
| WO | WO 2016/166442 A1 * | 10/2016 | ............... A61H 1/02 |
| WO | WO 2016/207855 A1 * | 12/2016 | ............... A61F 2/74 |

OTHER PUBLICATIONS

U.S. Appl. No. 15/082,824, filed Mar. 28, 2016.
U.S. Appl. No. 14/577,524, filed Dec. 19, 2014.
U.S. Appl. No. 15/823,523, filed Nov. 17, 2017.
U.S. Appl. No. 15/887,866, filed Feb. 2, 2018.
International Search Report and Written Opinion dated Apr. 26, 2018, International Patent Application No. PCT/US2018/016729, filed Feb. 2, 2018, 7 pages.
International Search Report and Written Opinion dated Jul. 18, 2016, International Patent Application No. PCT/US2016/024366, filed Mar. 25, 2016, 7 pages.
International Search Report and Written Opinion dated Jul. 19, 2018, International Patent Application No. PCT/US2018/027643, filed Apr. 13, 2018, 7 pages.
Taniguchi, "Flexible Artificial Muscle Actuator Using Coiled Shape 5 Memory Alloy Wires," APCBEE Procedia 7:54-59, Jan. 1, 2013.
International Search Report and Written Opinion dated Dec. 6, 2018, Patent Application No. PCT/US2018/048639, 7 pages.
Tamez-Duque et al., "Real-time strap pressure sensor system for powered exoskeletons," Sensors 15(2):4550-4563, Feb. 2015.
International Search Report and Written Opinion dated Mar. 30, 2021, Patent Application No. PCT/US2020/064647, 10 pages.

* cited by examiner

LEG EXOSKELETON SYSTEM AND METHOD

CROSS-REFERENCE TO RELATED APPLICATIONS

This application is a non-provisional of and claims the benefit of U.S. Provisional Application No. 62/485,279, filed Apr. 13, 2017 entitled "ADJUSTABLE FLUIDIC ACTUATOR SYSTEM AND METHOD," which application is hereby incorporated herein by reference in its entirety and for all purposes.

This application is also related to U.S. patent application Ser. No. 15/887,866, filed Feb. 2, 2018, entitled "SYSTEM AND METHOD FOR USER INTENT RECOGNITION," and is related to U.S. patent application Ser. No. 15/823,523, filed Nov. 27, 2017, entitled "PNEUMATIC EXOSKELETON SYSTEM AND METHOD," and is related to U.S. patent application Ser. No. 15/082,824, filed Mar. 28, 2016, entitled "LOWER-LEG EXOSKELETON SYSTEM AND METHOD," which applications are also hereby incorporated herein by reference in their entirety and for all purposes.

BRIEF DESCRIPTION OF THE DRAWINGS

FIG. 10b illustrates a side view of the pneumatic actuator of FIG. 10a in an expanded configuration showing the cross section of FIG. 10a.

FIG. 12 is an exemplary illustration of another embodiment of an actuator system architecture using a flexure as a pivot for the ribs and an actuator with a varying diameter comprising a smart material embedded with sensors that can be used to measure strain within the walls, measure actuator position, and the like.

Figure 1:
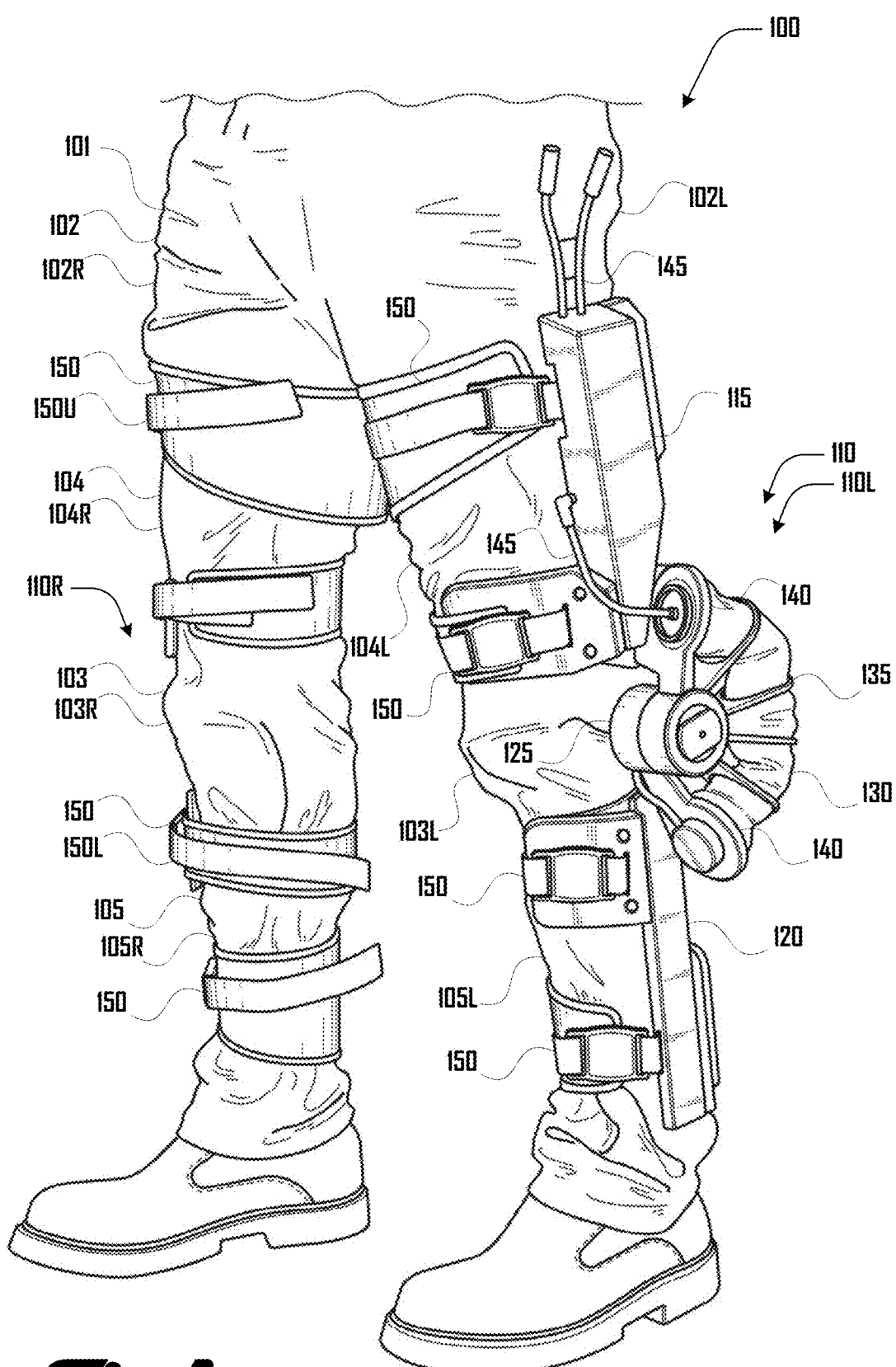
FIG. 1 is an example illustration of an embodiment of an exoskeleton system being worn by a user.

It should be noted that the figures are not drawn to scale and that elements of similar structures or functions are generally represented by like reference numerals for illustrative purposes throughout the figures. It also should be noted that the figures are only intended to facilitate the description of the preferred embodiments. The figures do not illustrate every aspect of the described embodiments and do not limit the scope of the present disclosure.

DETAILED DESCRIPTION

The present disclosure teaches example embodiments of a fluidic exoskeleton system that includes one or more adjustable fluidic actuators. Some preferred embodiments include a fluidic actuator that can be operated at various pressure levels with a large stroke length in a configuration that can be oriented with a joint on a human body.

Turning to FIG. 1, an example of an embodiment of an exoskeleton system 100 being worn by a human user 101 is illustrated. As shown in this example, the exoskeleton system 100 comprises a left and right leg actuator unit 110L, 110R that are respectively coupled to a left and right leg 102L, 102R of the user. In this example illustration, portions of the right leg actuator unit 110R are obscured by the right leg 102R; however, it should be clear that in various embodiments the left and right leg actuator units 110L, 110R can be substantially mirror images of each other.

The leg actuator units 110 can include an upper arm 115 and a lower arm 120 that are rotatably coupled via a joint 125. A bellows actuator 130 extends between plates 140 that are coupled at respective ends of the upper arm 115 and lower arm 120, with the plates 140 coupled to separate rotatable portions of the joint 125. A plurality of constraint ribs 135 extend from the joint 125 and encircle a portion of the bellows actuator 130 as described in more detail herein. One or more sets of pneumatic lines 145 can be coupled to the bellows actuator 130 to introduce and/or remove fluid from the bellows actuator 130 to cause the bellows actuator 130 to expand and contract as discussed herein.

The leg actuator units 110L, 110R can be respectively coupled about the legs 102L, 102R of the user 101 with the joints 125 positioned at the knees 103L, 103R of the user 101 with the upper arms 115 of the leg actuator units 110L, 110R being coupled about the upper legs portions 104L, 104R of the user 101 via one or more couplers 150 (e.g., straps that surround the legs 104). The lower arms 120 of the leg actuator units 110L, 110R can be coupled about the lower leg portions 105L, 105R of the user 101 via one or more couplers 150. As shown in the example of FIG. 1, an upper arm 115 can be coupled to the upper leg portion 104 of a leg 102 above the knee 103 via two couplers 150 and the lower arm 120 can be coupled to the lower leg portion 105 of a leg 102 below the knee 103 via two couplers 150. It is important to note that some of these components can be omitted in certain embodiments, some of which are discussed within. Additionally, in further embodiments, one or more of the components discussed herein can be operably replaced by an alternative structure to produce the same functionality.

Figure 2:
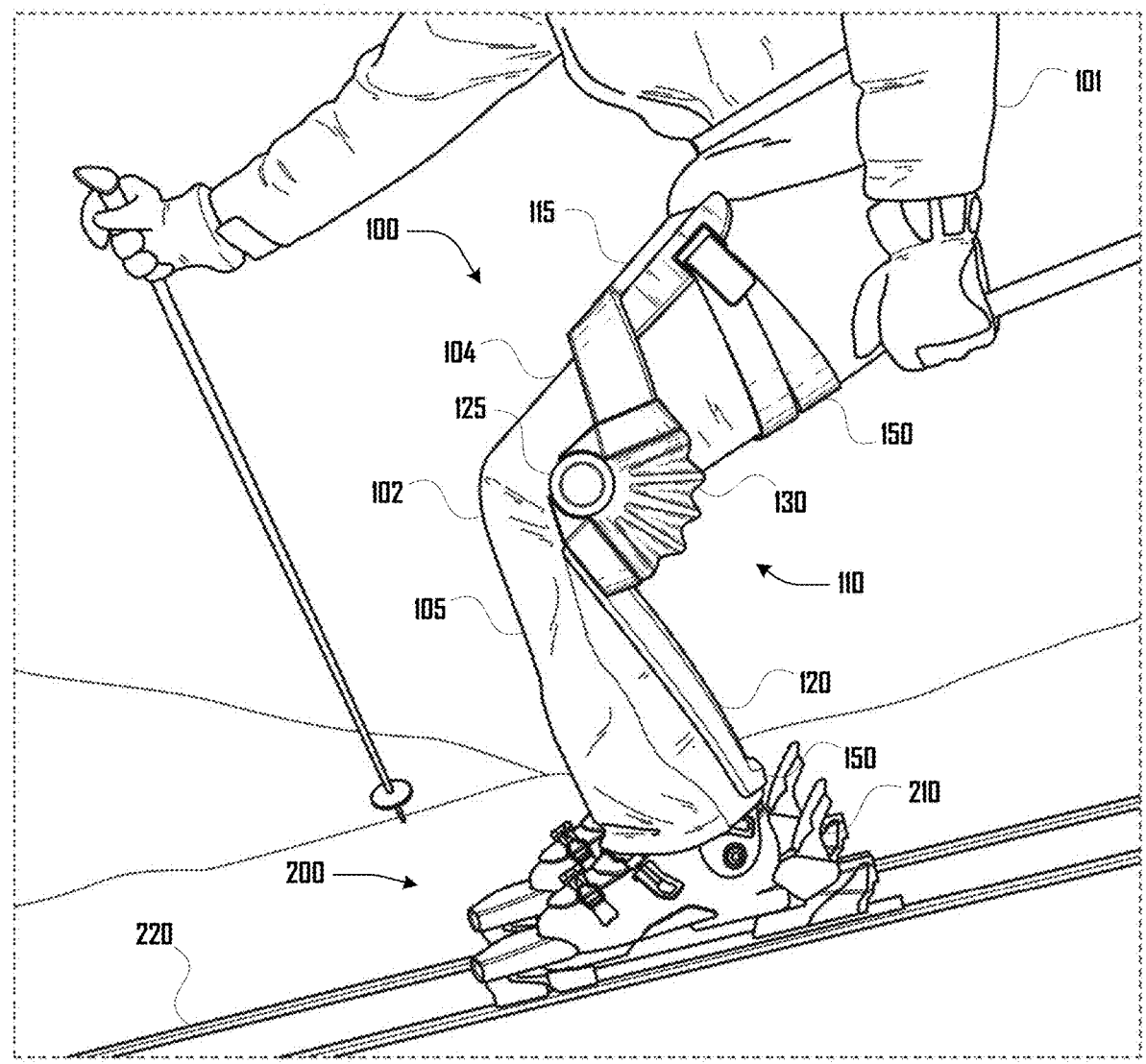
FIG. 2 is an example illustration of another embodiment of an exoskeleton system being worn by a user while skiing.
Figure 3:
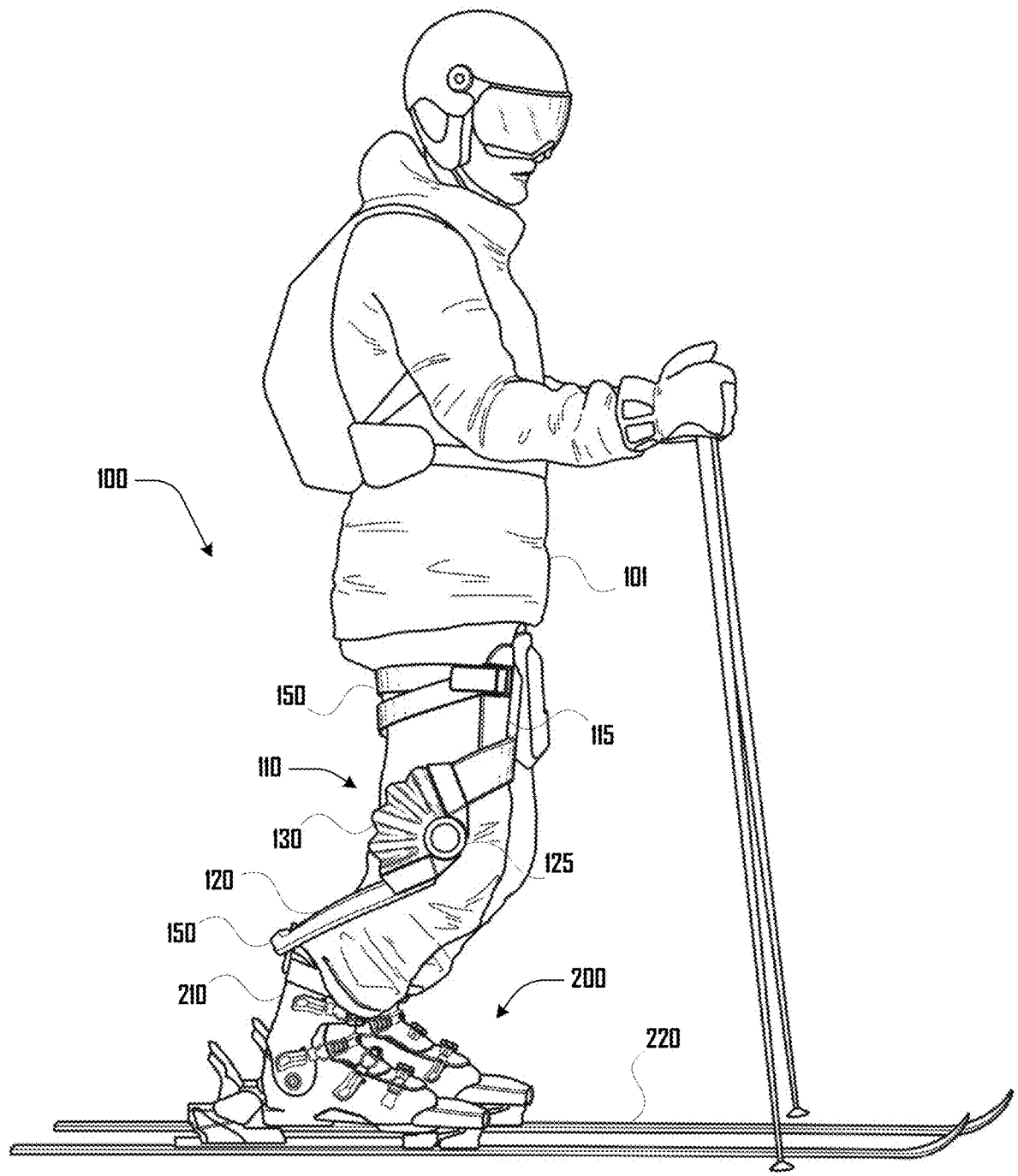
FIG. 3 is an example illustration of a further embodiment of an exoskeleton system being worn by a user while skiing.

As discussed herein, an exoskeleton system 100 can be configured for various suitable uses. For example, FIGS. 2 and 3 illustrate an exoskeleton system 100 being used by a user during skiing. As shown in FIGS. 2 and 3 the user can wear the exoskeleton system 100 and a skiing assembly 200 that includes a pair of ski boots 210 and pair of skis 220. In various embodiments, the lower arms 120 of the leg actuator units 110 can be removably coupled to the ski boots 210 via a coupler 150. Such embodiments can be desirable for directing force from the leg actuator units 110 to the skiing assembly. For example, as shown in FIGS. 2 and 3, a coupler 150 at the distal end of the lower arm 120 can couple the leg actuator unit 110 to the ski boot 210 and a coupler 150 at the distal end of the upper arm 115 can couple the leg actuator unit 110 to the upper leg 104 of the user 101.

Figure 4A:
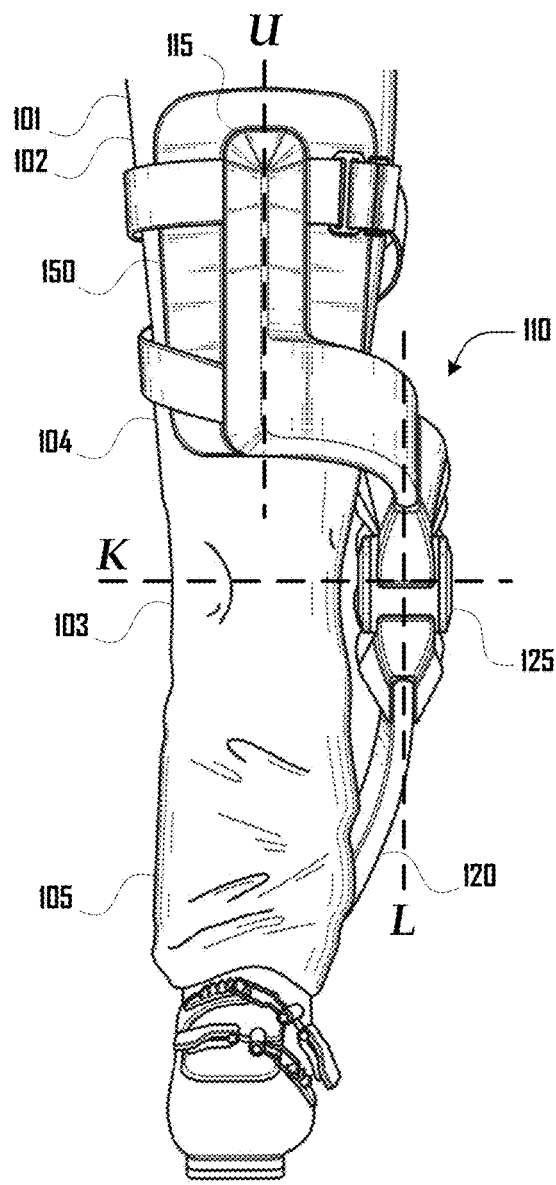
FIGS. 4a and 4b are example illustrations of a still further embodiment of an exoskeleton system being worn on the leg of a user.
Figure 4B:
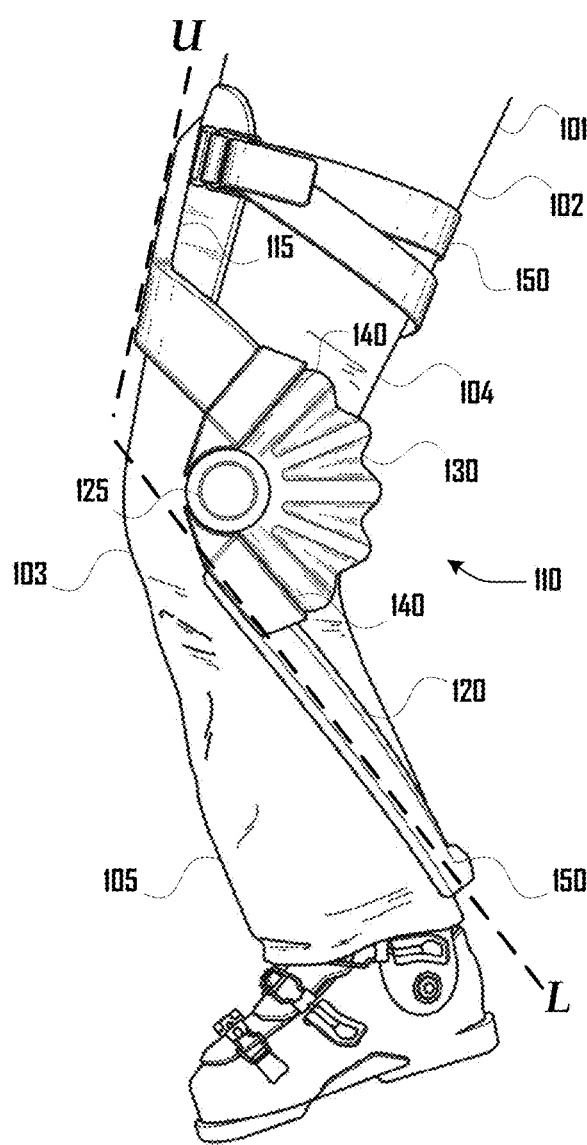

The upper and lower arms 115, 120 of a leg actuator unit 110 can be coupled to the leg 102 of a user 101 in various suitable ways. For example, FIG. 1 illustrates an example where the upper and lower arms 115, 120 and joint 125 of the leg actuator unit 110 are coupled along lateral faces of the top and bottom portions 104, 105 of the leg 102. FIGS. 4a and 4b illustrate another example of an exoskeleton system 100 where the joint 125 is disposed laterally and adjacent to the knee 103 with a rotational axis K of the joint 125 being disposed coincident with a rotational axis of the knee 103. The upper arm 115 can extend from the joint 125 along a lateral face of the upper leg 104 to an anterior face of the upper leg 104. The portion of the upper arm 115 on the anterior face of the upper leg 104 can extend along an axis U. The lower arm 120 can extend from the joint 125 along a lateral face of the lower leg 105 from a medial location at the joint 125 to a posterior location at a bottom end of the lower leg 105 with a portion extending along axis L that is perpendicular to axis K.

In various embodiments, the joint structure 125 can constrain the bellows actuator 130 such that force created by actuator fluid pressure within the bellows actuator 130 can be directed about an instantaneous center (which may or may not be fixed in space). In some cases of a revolute or rotary joint, or a body sliding on a curved surface, this instantaneous center can coincide with the instantaneous center of rotation of the joint 125 or a curved surface. Forces created by a leg actuator unit 110 about a rotary joint 125 can be used to apply a moment about an instantaneous center as well as still be used to apply a directed force. In some cases of a prismatic or linear joint (e.g., a slide on a rail, or the like), the instantaneous center can be kinematically considered to be located at infinity, in which case the force directed about this infinite instantaneous center can be considered as a force directed along the axis of motion of the prismatic joint. In various embodiments, it can be sufficient for a rotary joint 125 to be constructed from a mechanical pivot mechanism. In such an embodiment, the joint 125 can have a fixed center of rotation that can be easy to define, and the bellows actuator 130 can move relative to the joint 125. In a further embodiment, it can be beneficial for the joint 125 to comprise a complex linkage that does not have a single fixed center of rotation. In yet another embodiment, the joint 125 can comprise a flexure design that does not have a fixed joint pivot. In still further embodiments, the joint 125 can comprise a structure, such as a human joint, robotic joint, or the like.

In various embodiments, leg actuator unit 110 (e.g., comprising bellows actuator 130, joint structure 125, constraint ribs 135 and the like) can be integrated into a system to use the generated directed force of the leg actuator unit 110 to accomplish various tasks. In some examples, a leg actuator unit 110 can have one or more unique benefits when the leg actuator unit 110 is configured to assist the human body or is included into a powered exoskeleton system 100. In an example embodiment, the leg actuator unit 110 can be configured to assist the motion of a human user about the user's knee joint 103. To do so, in some examples, the instantaneous center of the leg actuator unit 110 can be designed to coincide or nearly coincide with the instantaneous center of rotation of the knee (e.g., aligned along common axis K as shown in FIG. 4a). In one example configuration, the leg actuator unit 110 can be positioned lateral to the knee joint 103 as shown in FIGS. 1, 2, 3, and 4a (as opposed to in front or behind). In another example configuration, the leg actuator unit 110 can be positioned behind the knee 103, in front of the knee 103, on the inside of the knee 103, or the like. In various examples, the human knee joint 103 can function as (e.g., in addition to or in place of) the joint 125 of the leg actuator unit 110.

For clarity, example embodiments discussed herein should not be viewed as a limitation of the potential applications of the leg actuator unit 110 described within this disclosure. The leg actuator unit 110 can be used on other joints of the body including but not limited to the elbow, hip, finger, spine, or neck, and in some embodiments, the leg actuator unit 110 can be used in applications that are not on the human body such as in robotics, for general purpose actuation, or the like.

Some embodiments can apply a configuration of a leg actuator unit 110 as described herein for linear actuation applications. In an example embodiment, the bellows 130 can comprise a two-layer impermeable/inextensible construction, and one end of the constraining ribs 135 can be fixed to the bellows 135 at predetermined positions. The joint structure 125 in various embodiments can be configured as a series of slides on a pair of linear guide rails, where the remaining end of each constraining rib 135 is connected to a slide. The motion and force of the fluidic actuator can therefore be constrained and directed along the linear rail.

Figure 5:
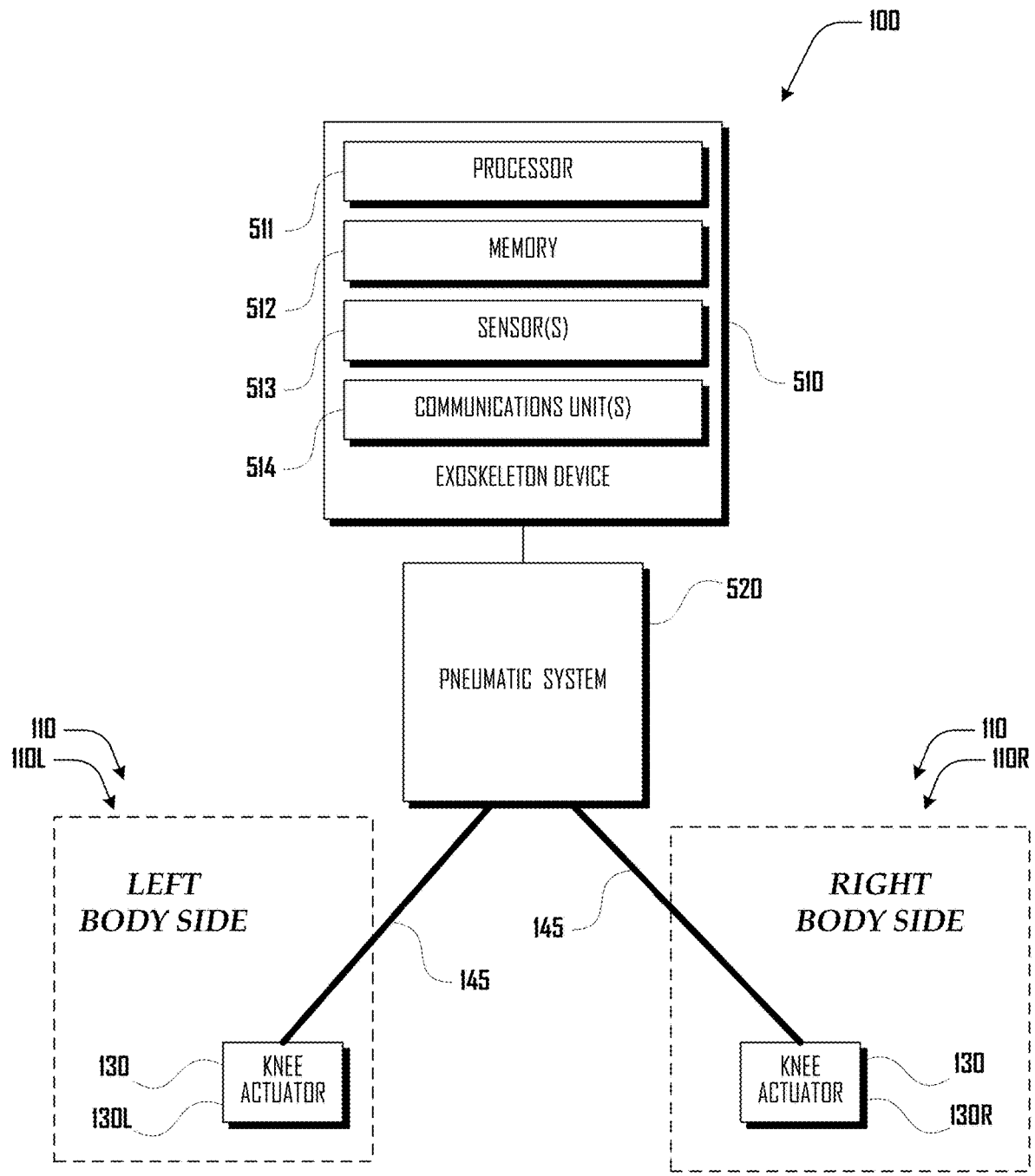
FIG. 5 is a block diagram illustrating an embodiment of an exoskeleton system.

FIG. 5 is a block diagram of an example embodiment of an exoskeleton system 100 that includes an exoskeleton device 510 that is operably connected to a pneumatic system 520. The exoskeleton device 510 comprises a processor 511, a memory 512, one or more sensors 513 and a communication unit 514. A plurality of actuators 130 are operably coupled to the pneumatic system 520 via respective pneumatic lines 145. The plurality of actuators 130 include a pair knee-actuators 130L, 130R that are positioned on the right and left side of a body 100. For example, as discussed above, the example exoskeleton system 100 shown in FIG. 5 can comprise a left and right leg actuator unit 110L, 110R on respective sides of the body 101 as shown in FIGS. 1-3.

In various embodiments, the example system 100 can be configured to move and/or enhance movement of the user wearing the exoskeleton system 100. For example, the exoskeleton device 510 can provide instructions to the pneumatic system 520, which can selectively inflate and/or deflate the bellows actuators 130 via pneumatic lines 145. Such selective inflation and/or deflation of the bellows actuators 130 can move one or both legs 102 to generate and/or augment body motions such as walking, running, jumping, climbing, lifting, throwing, squatting, skiing or the like. In further embodiments, the pneumatic system 520 can be manually controlled, configured to apply a constant pressure, or operated in any other suitable manner.

In some embodiments, such movements can be controlled and/or programmed by the user 101 that is wearing the exoskeleton system 100 or by another person. In some embodiments, the exoskeleton system 100 can be controlled by movement of the user. For example, the exoskeleton device 510 can sense that the user is walking and carrying a load and can provide a powered assist to the user via the actuators 130 to reduce the exertion associated with the load and walking. Similarly, where a user 101 wears the exoskeleton system 100 while skiing, the exoskeleton system 100 can sense movements of the user 101 (e.g., made by the user 101, in response to terrain, or the like) and can provide a powered assist to the user via the actuators 130 to enhance or provide an assist to the user while skiing.

Accordingly, in various embodiments, the exoskeleton system 130 can react automatically without direct user interaction. In further embodiments, movements can be controlled in real-time by a controller, joystick or thought control. Additionally, some movements can be pre-preprogrammed and selectively triggered (e.g., walk forward, sit, crouch) instead of being completely controlled. In some embodiments, movements can be controlled by generalized instructions (e.g. walk from point A to point B, pick up box from shelf A and move to shelf B).

In various embodiments, the exoskeleton device 100 can be operable to perform methods or portions of methods described in more detail below or in related applications incorporated herein by reference. For example, the memory 512 can include non-transient computer readable instructions, which if executed by the processor 511, can cause the exoskeleton system 100 to perform methods or portions of methods described herein or in related applications incorporated herein by reference. The communication unit 514 can include hardware and/or software that allows the exoskeleton system 100 to communicate with other devices, including a user device, a classification server, other exoskeleton systems, or the like, directly or via a network.

In some embodiments, the sensors 513 can include any suitable type of sensor, and the sensors 513 can be located at a central location or can be distributed about the exoskeleton system 100. For example, in some embodiments, the exoskeleton system 100 can comprise a plurality of accelerometers, force sensors, position sensors, and the like, at various suitable positions, including at the arms 115, 120, joint 125, actuators 130 or any other location. Accordingly, in some examples, sensor data can correspond to a physical state of one or more actuators 130, a physical state of a portion of the exoskeleton system 100, a physical state of the exoskeleton system 100 generally, and the like. In some embodiments, the exoskeleton system 100 can include a global positioning system (GPS), camera, range sensing system, environmental sensors, or the like.

The pneumatic system 520 can comprise any suitable device or system that is operable to inflate and/or deflate the actuators 130 individually or as a group. For example, in one embodiment, the pneumatic system can comprise a diaphragm compressor as disclosed in related patent application Ser. No. 14/577,817 filed Dec. 19, 2014.

As discussed herein, various suitable exoskeleton systems 100 can be used in various suitable ways and for various suitable applications. However, such examples should not be construed to be limiting on the wide variety of exoskeleton systems 100 or portions thereof that are within the scope and spirit of the present disclosure. Accordingly, exoskeleton systems 100 that are more or less complex than the examples of FIGS. 1, 2, 3, 4a, 4b and 5 are within the scope of the present disclosure.

Additionally, while various examples relate to an exoskeleton system 100 associated with the legs or lower body of a user, further examples can be related to any suitable portion of a user body including the torso, arms, head, legs, or the like. Also, while various examples relate to exoskeletons, it should be clear that the present disclosure can be applied to other similar types of technology, including prosthetics, body implants, robots, or the like. Further, while some examples can relate to human users, other examples can relate to animal users, robot users, various forms of machinery, or the like.

Figure 6A:
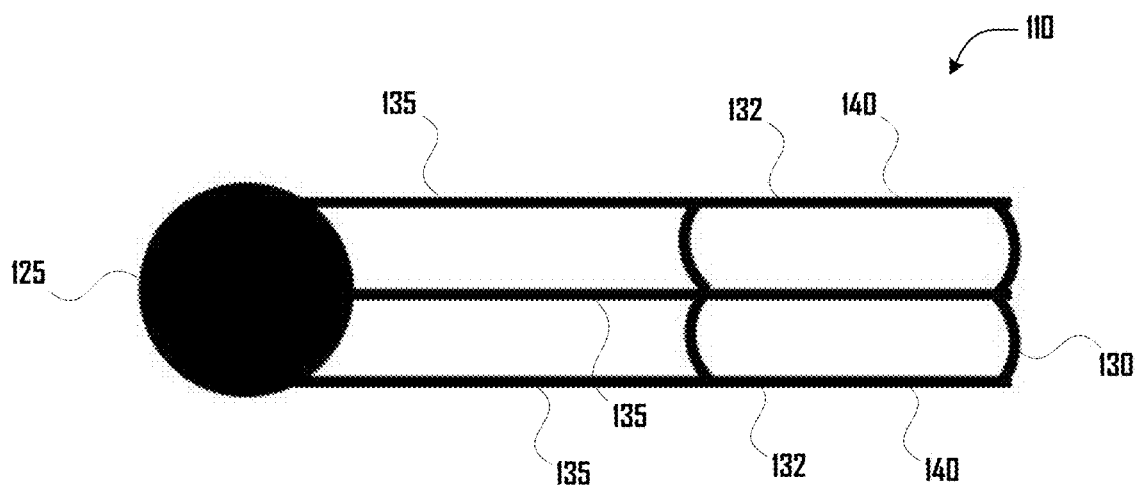
FIG. 6a illustrates a side view of a pneumatic actuator in a compressed configuration in accordance with one embodiment.
Figure 6B:
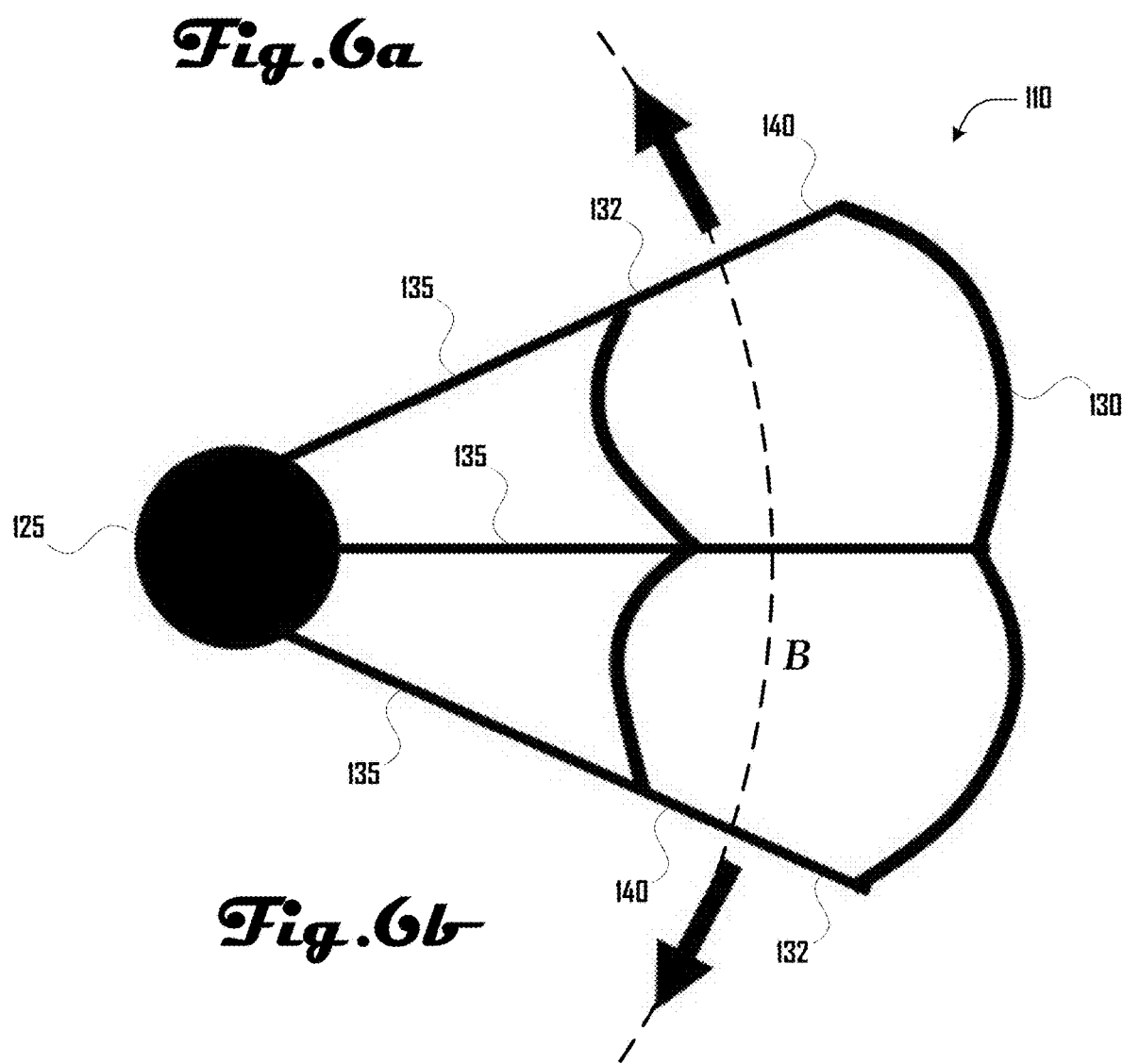
FIG. 6b illustrates a side view of the pneumatic actuator of FIG. 6a in an expanded configuration.
Figure 7A:
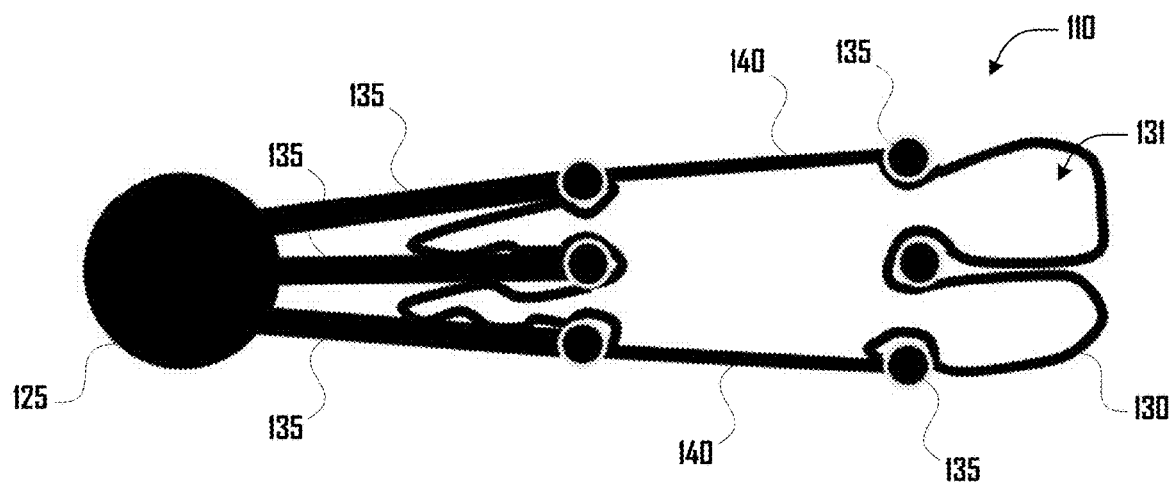
FIG. 7a illustrates a cross-sectional side view of a pneumatic actuator in a compressed configuration in accordance with another embodiment.
Figure 7B:
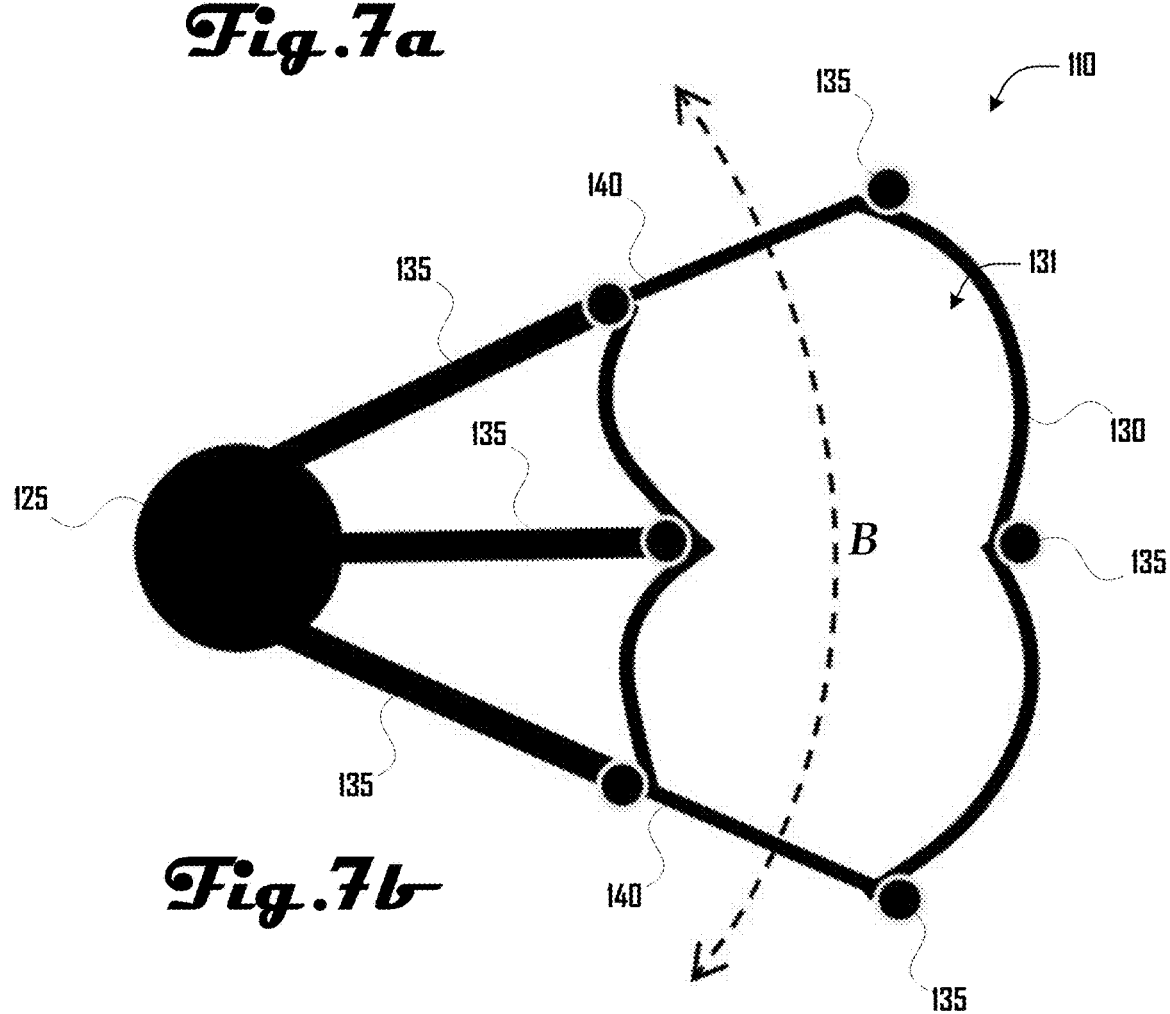
FIG. 7b illustrates a cross-sectional side view of the pneumatic actuator of FIG. 7a in an expanded configuration.

Turning to FIGS. 6a, 6b, 7a and 7b, examples of a leg actuator unit 110 including the joint 125, bellows 130, constraint ribs 135, and base plates 140. More specifically, FIG. 6a illustrates a side view of a leg actuator unit 110 in a compressed configuration and FIG. 6b illustrates a side view of the leg actuator unit 110 of FIG. 6a in an expanded configuration. FIG. 7a illustrates a cross-sectional side view of a leg actuator unit 110 in a compressed configuration and FIG. 7b illustrates a cross-sectional side view of the leg actuator unit 110 of FIG. 7a in an expanded configuration.

As shown in FIGS. 6a, 6b, 7a and 7b, the joint 125 can have a plurality of constraint ribs 135 extending from and coupled to the joint 125, which surround or abut a portion of the bellows 130. For example, in some embodiments, constraint ribs 135 can abut the ends 132 of the bellows 130 and can define some or all of the base plates 140 that the ends 132 of the bellows 130 can push against. However, in some examples, the base plates 140 can be separate and/or different elements than the constraint ribs 135 (e.g., as shown in FIG. 1). Additionally, one or more constraint ribs 135 can be disposed between ends 132 of the bellows 130. For example, FIGS. 6a, 6b, 7a and 7b illustrate one constraint rib 135 disposed between ends 132 of the bellows 130 and FIG. 1 illustrates four constraint ribs 135 disposed between ends 132 of the bellows 130. Further embodiments can include any suitable number of constraint ribs 135 disposed between ends of the bellows 130, including 1, 2, 3, 4, 5, 6, 7, 8, 9, 10, 15, 20, 25, 30, 50, 100 and the like.

As shown in cross sections of FIGS. 7a and 7b, the bellows 130 can define a cavity 131 that can be filled with fluid (e.g., air), to expand the bellow 130, which can cause the bellows to elongate along axis B as shown in FIGS. 6b and 7b. For example, increasing a pressure and/or volume of fluid in the bellows 130 shown in FIG. 6a can cause the bellows 130 to expand to the configuration shown in FIG. 6b. Similarly, increasing a pressure and/or volume of fluid in the bellows 130 shown in FIG. 7a can cause the bellows 130 to expand to the configuration shown in FIG. 7b. For clarity, the use of the term 'bellows' is to describe a component in the described actuator unit 110 and is not intended to limit the geometry of the component. The bellows 130 can be constructed with a variety of geometries including but not limited to: a constant cylindrical tube, a cylinder of varying cross-sectional area, a 3-D woven geometry that inflates to a defined arc shape, and the like.

Alternatively, decreasing a pressure and/or volume of fluid in the bellows 130 shown in FIG. 6b can cause the bellows 130 to contract to the configuration shown in FIG. 6a. Similarly, decreasing a pressure and/or volume of fluid in the bellows 130 shown in FIG. 7b can cause the bellows 130 to contract to the configuration shown in FIG. 7a. Such increasing or decreasing of a pressure or volume of fluid in the bellows 130 can be performed by pneumatic system 520 and pneumatic lines 145 of the exoskeleton system 100, which can be controlled by the exoskeleton device 510 (see FIG. 5).

In one preferred embodiment, the bellows 130 can be inflated with air; however, in further embodiments, any suitable fluid can be used to inflate the bellows 130. For example, gasses including oxygen, helium, nitrogen, and/or argon, or the like can be used to inflate and/or deflate the bellows 130. In further embodiments, a liquid such as water, an oil, or the like can be used to inflate the bellows 130. Additionally, while some examples discussed herein relate to introducing and removing fluid from a bellows 130 to change the pressure within the bellows 130, further examples can include heating and/or cooling a fluid to modify a pressure within the bellows 130.

As shown in FIGS. 6a, 6b, 7a and 7b, the constraint ribs 135 can support and constrain the bellows 130. For example, inflating the bellows 130 cause the bellows 130 expand along a length of the bellows 130 and also cause the bellows 130 to expand radially. The constraint ribs 135 can constrain radial expansion of a portion of the bellows 130. Additionally, as discussed herein, the bellows 130 comprise a material that is flexible in one or more directions and the constraint ribs 135 can control the direction of linear expansion of the bellows 130. For example, in some embodiments, without constraint ribs 135 or other constraint structures the bellows 130 would herniate or bend out of axis uncontrollably such that suitable force would not be applied to the base plates 140 such that the arms 115, 120 would not be suitably or controllably actuated. Accordingly, in various embodiments, the constraint ribs 135 can be desirable to generate a consistent and controllable axis of expansion B for the bellows 130 as they are inflated and/or deflated.

In some examples, the bellows 130 in a deflated configuration can substantially extend past a radial edge of the constraint ribs 135 and can retract during inflation to extend less past the radial edge of the constraint ribs 135, to extend to the radial edge of the constraint ribs 135, or to not extend less past the radial edge of the constraint ribs 135. For example, FIG. 7a illustrates a compressed configuration of the bellows 130 where the bellows 130 substantially extend past a radial edge of the constraint ribs 135 and FIG. 7b illustrates the bellows 130 retracting during inflation to extend less past the radial edge of the constraint ribs 135 in an inflated configuration of the bellows 130.

Figure 8A:
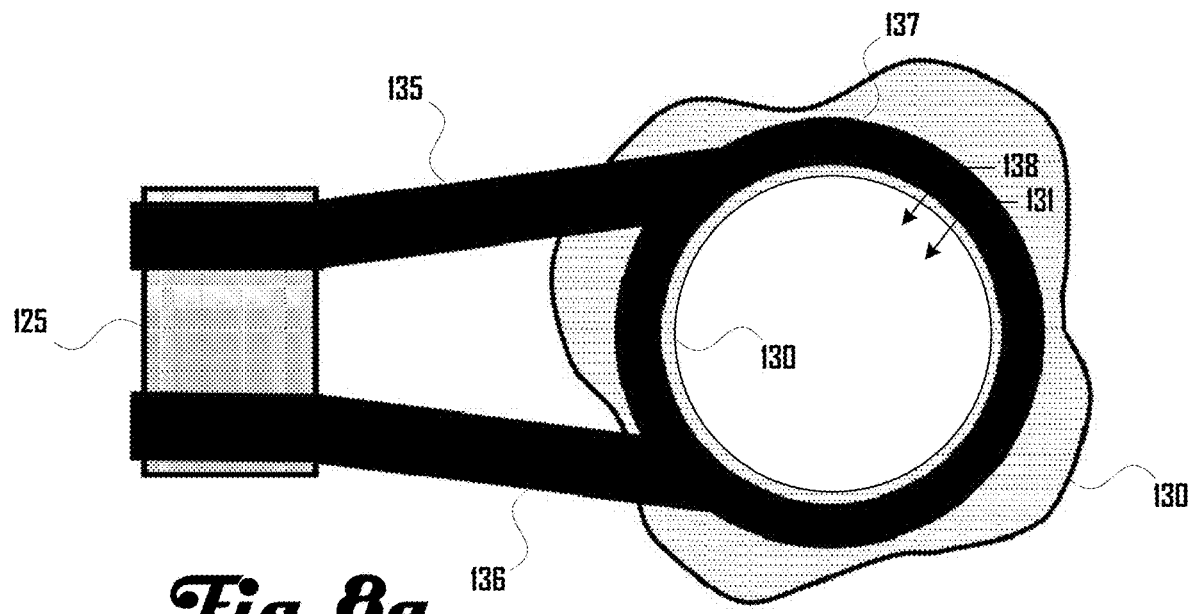
FIG. 8a illustrates a top view of a pneumatic actuator in a compressed configuration in accordance with another embodiment.
Figure 8B:
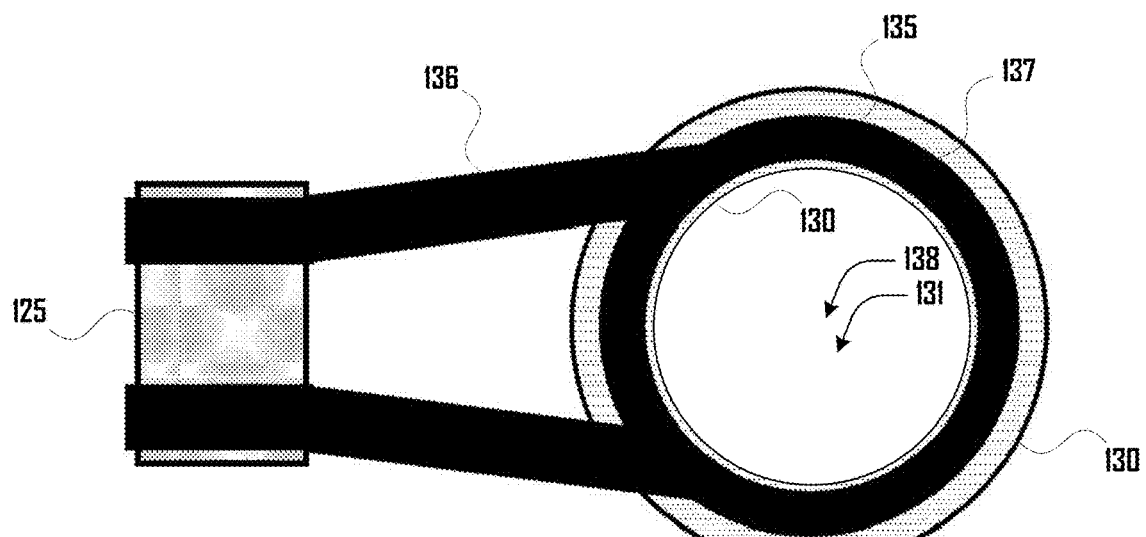
FIG. 8b illustrates a top of the pneumatic actuator of FIG. 8a in an expanded configuration.

Similarly, FIG. 8a illustrates a top view of a compressed configuration of bellows 130 where the bellows 130 substantially extend past a radial edge of constraint ribs 135 and FIG. 8b illustrates a top view where the bellows 130 retract during inflation to extend less past the radial edge of the constraint ribs 135 in an inflated configuration of the bellows 130.

Figure 9:
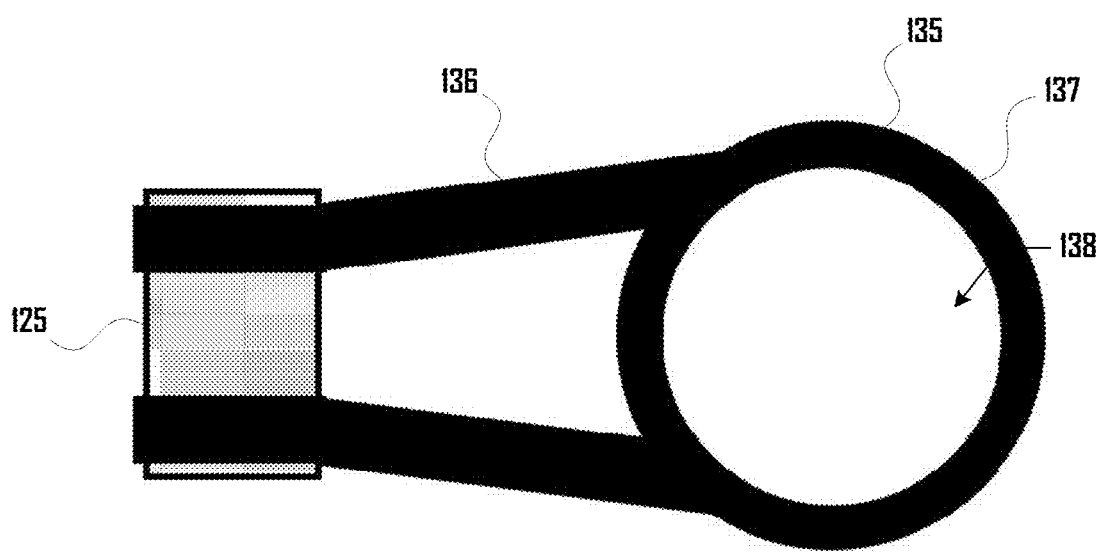
FIG. 9 illustrates a top view of a pneumatic actuator constraint rib in accordance with an embodiment.

Constraint ribs 135 can be configured in various suitable ways. For example, FIGS. 8a, 8b and 9 illustrate a top view of an example embodiment of a constraint rib 135 having a pair of rib arms 136 that extend from the joint 125 and couple with a circular rib ring 137 that defines a rib cavity 138 through which a portion of the bellows 130 can extend (e.g., as shown in FIGS. 7a, 7b, 8a and 8b). In various examples, the one or more constraint ribs 135 can be a substantially planar element with the rib arms 136 and rib ring 137 being disposed within a common plane.

In further embodiments, the one or more constraint ribs 135 can have any other suitable configuration. For example, some embodiments can have any suitable number of rib arms 136, including one, two, three, four, five, or the like. Additionally, the rib ring 137 can have various suitable shapes and need not be circular, including one or both of an inner edge that defines the rib cavity 138 or an outer edge of the rib ring 137.

In various embodiments, the constraining ribs 135 can be configured to direct the motion of the bellows 130 through a swept path about some instantaneous center (which may or may not be fixed in space) and/or to prevent motion of the bellows 130 in undesired directions, such as out-of-plane buckling. As a result, the number of constraining ribs 135 included in some embodiments can vary depending on the specific geometry and loading of the leg actuator unit 110. Examples can range from one constraining rib 135 up to any suitable number of constraining ribs 135; according, the number of constraining ribs 135 should not be taken to limit the applicability of the invention.

The one or more constraining ribs 135 can be constructed in a variety of ways. For example the one or more constraining ribs 135 can vary in construction on a given leg actuator unit 110, and/or may or may not require attachment to the joint structure 125. In various embodiments, the constraining ribs 135 can be constructed as an integral component of a central rotary joint structure 125. An example embodiment of such a structure can include a mechanical rotary pin joint, where the constraining ribs 135 are connected to and can pivot about the joint 125 at one end of the joint 125, and are attached to an inextensible outer layer of the bellows 130 at the other end. In another set of embodiments, the constraining ribs 135 can be constructed in the form of a single flexural structure that directs the motion of the bellows 130 throughout the range of motion for the leg actuator unit 110. Another example embodiment uses a flexural constraining rib 135 that is not connected integrally to the joint structure 125 but is instead attached externally to a previously assembled joint structure 125. Another example embodiment can comprise the constraint rib 125 being composed of pieces of fabric wrapped around the bellows 130 and attached to the joint structure 125, acting like a hammock to restrict and/or guide the motion of the bellows 130. There are additional methods available for constructing the constraining ribs 135 that can be used in additional embodiments that include but are not limited to a linkage, a rotational flexure connected around the joint 125, and the like.

In some examples, a design consideration for constraining ribs 135 can be how the one or more constraining ribs 125 interact with the bellows 130 to guide the path of the bellows 130. In various embodiments, the constraining ribs 135 can be fixed to the bellows 130 at predefined locations along the length of the bellows 130. One or more constraining ribs 135 can be coupled to the bellows 130 in various suitable ways, including but not limited to sewing, mechanical clamps, geometric interference, direct integration, and the like. In other embodiments, the constraining ribs 135 can be configured such that the constraining ribs 135 float along the length of the bellows 130 and are not fixed to the bellows 130 at predetermined connection points. In some embodiments, the constraining ribs 135 can be configured to restrict a cross sectional area of the bellows 130. An example embodiment can include a tubular bellows 130 attached to a constraining rib 135 that has an oval cross section, which in some examples can be a configuration to reduce the width of the bellows 130 at that location when the bellows 130 is inflated.

The bellows 130 can have various functions in some embodiments, including containing operating fluid of the leg actuator unit 110, resisting forces associated with operating pressure of the leg actuator unit 110, and the like. In various examples, the leg actuator unit 110 can operate at a fluid pressure above, below or at about ambient pressure. In various embodiments, bellows 130 can comprise one or more flexible, yet inextensible or practically inextensible materials in order to resist expansion (e.g., beyond what is desired in directions other than an intended direction of force application or motion) of the bellows 130 beyond what is desired when pressurized above ambient pressure. Additionally, the bellows 130 can comprise an impermeable or semi-impermeable material in order to contain the actuator fluid.

Figure 11:
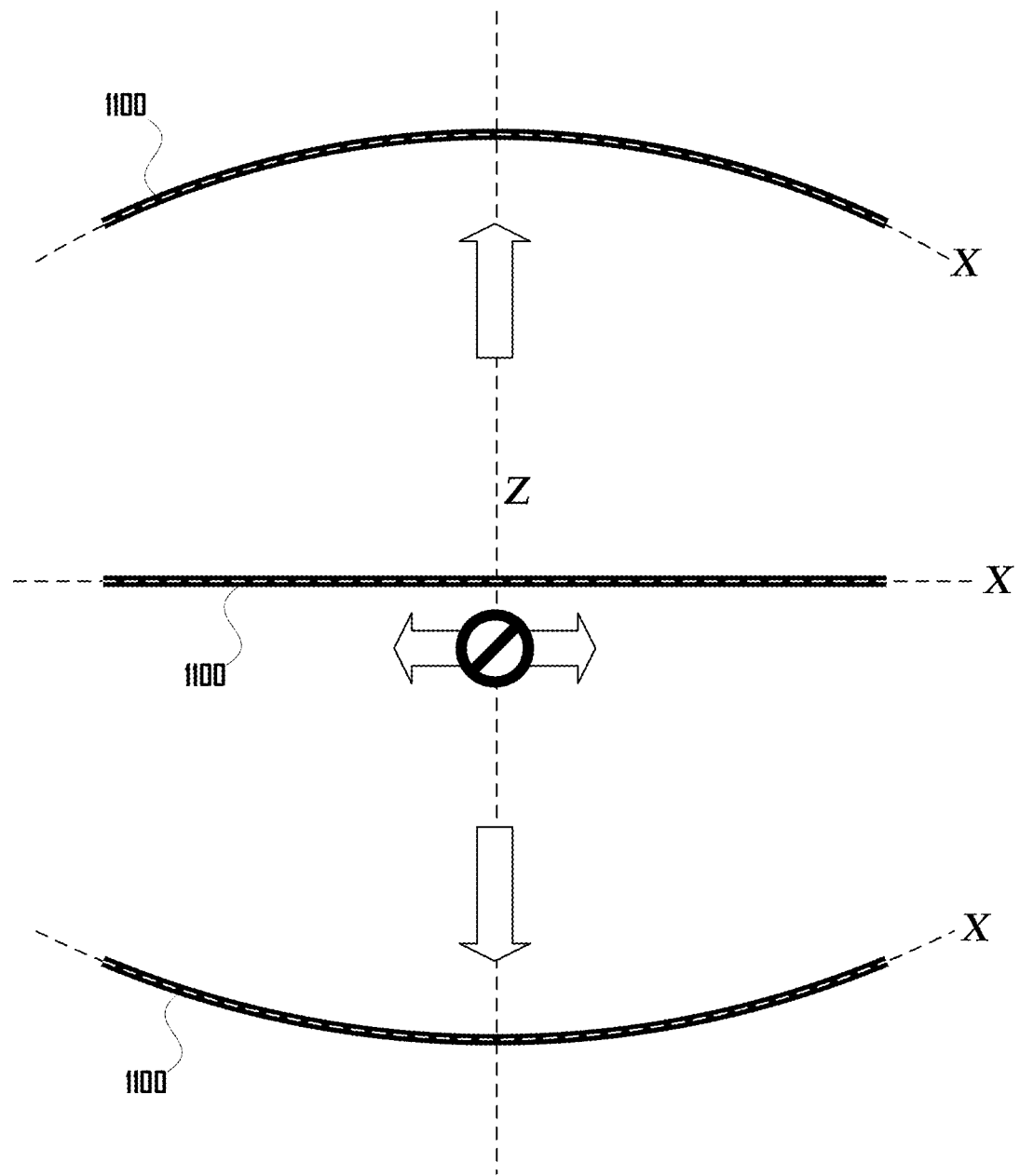
FIG. 11 illustrates an example planar material that is substantially inextensible along one or more plane axes of the planar material while being flexible in other directions.

For example, in some embodiments, the bellows 130 can comprise a flexible sheet material such as woven nylon, rubber, polychloroprene, a plastic, latex, a fabric, or the like. Accordingly, in some embodiments, bellows 130 can be made of a planar material that is substantially inextensible along one or more plane axes of the planar material while being flexible in other directions. For example, FIG. 11 illustrates a side view of a planar material 1100 (e.g., a fabric) that is substantially inextensible along axis X that is coincident with the plane of the material 1100, yet flexible in other directions, including axis Z. In the example of FIG. 11, the material 1100 is shown flexing upward and downward along axis Z while being inextensible along axis X. In various embodiments, the material 1100 can also be inextensible along an axis Y (not shown) that is also coincident with the plane of the material 1100 like axis X and perpendicular to axis X.

In some embodiments, the bellows 130 can be made of a non-planar woven material that is inextensible along one or more axes of the material. For example, in one embodiment the bellows 130 can comprise a woven fabric tube. Woven fabric material can provide inextensibility along the length of the bellows 130 and in the circumferential direction. Such embodiments can still able to be configured along the body of the user 101 to align with the axis of a desired joint on the body 101 (e.g., the knee 103).

In various embodiments, the bellows 130 can develop its resulting force by using a constrained internal surface length and/or external surface length that are a constrained distance away from each other (e.g. due to an inextensible material as discussed above). In some examples, such a design can allow the actuator to contract on bellows 130, but when pressurized to a certain threshold, the bellows 130 can direct the forces axially by pressing on the plates 140 of the leg actuator unit 110 because there is no ability for the bellows 130 to expand further in volume otherwise due to being unable to extend its length past a maximum length defined by the body of the bellows 130.

Figure 10A:
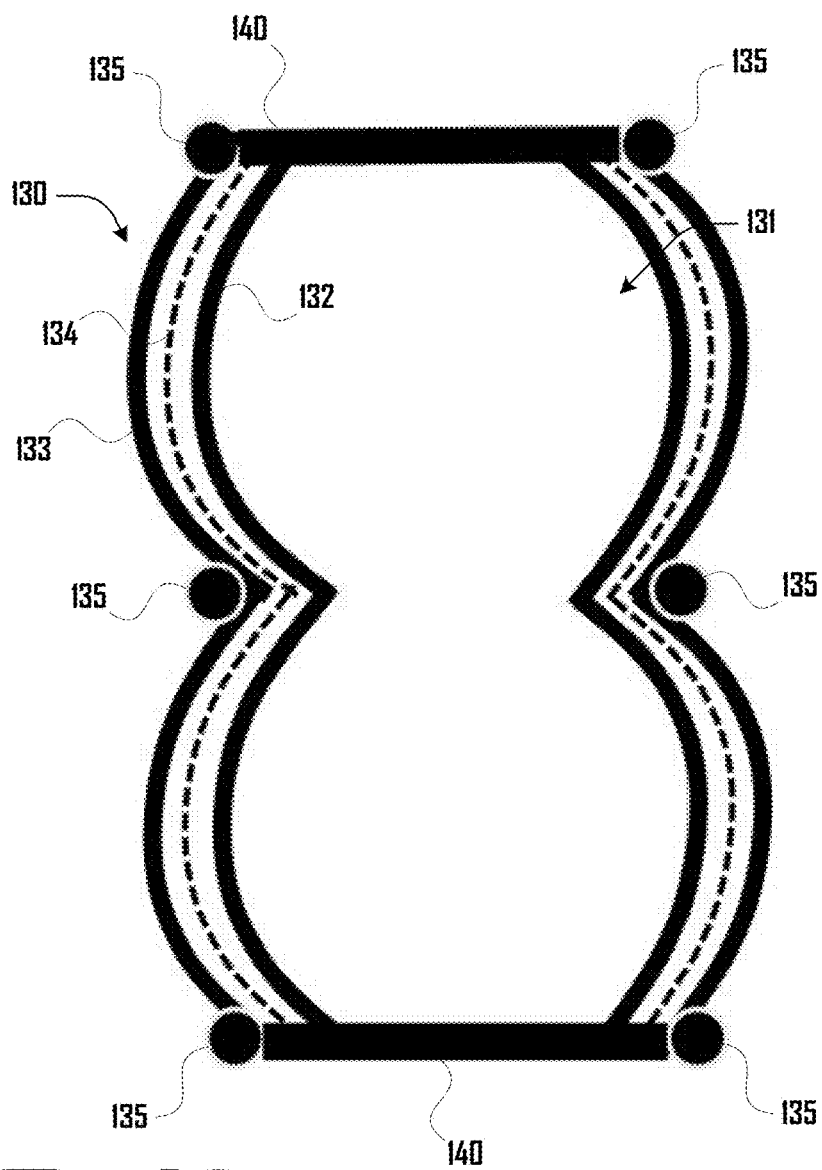
FIG. 10a illustrates a cross-sectional view of a pneumatic actuator bellows in accordance with another embodiment.
Figure 10B:
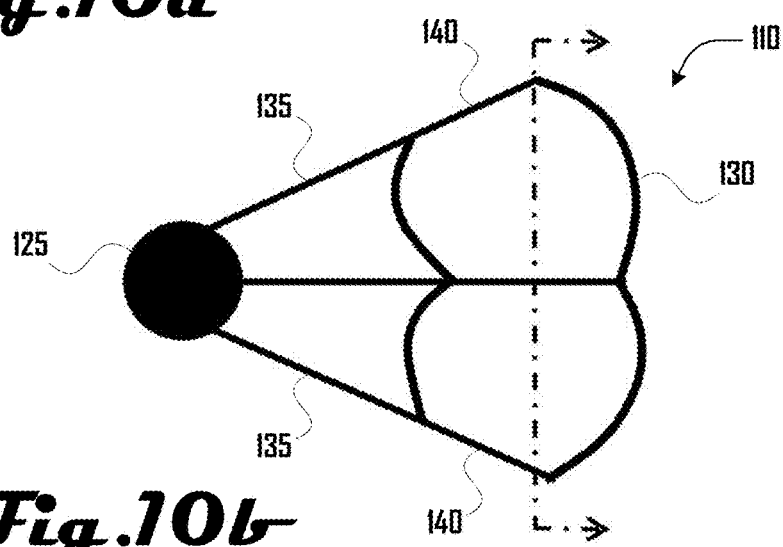

FIG. 10*a* illustrates a cross-sectional view of a pneumatic actuator unit 110 including bellows 130 in accordance with another embodiment and FIG. 10*b* illustrates a side view of the pneumatic actuator unit 110 of FIG. 10*a* in an expanded configuration showing the cross section of FIG. 10*a*. As shown in FIG. 10*a*, the bellows 130 can comprise an internal first layer 132 that defines the bellows cavity 131 and can comprise an outer second layer 133 with a third layer 134 disposed between the first and second layers 132, 133. Throughout this description, the use of the term 'layer' to describe the construction of the bellows 130 should not be viewed as limiting to the design. The use of 'layer' can refer to a variety of designs including but not limited to: a planar material sheet, a wet film, a dry film, a rubberized coating, a co-molded structure, and the like.

In some examples, the internal first layer 132 can comprise a material that is impermeable or semi-permeable to the actuator fluid (e.g., air) and the external second layer 133 can comprise an inextensible material as discussed herein. For example, as discussed herein, an impermeable layer can refer to an impermeable or semi-permeable layer and an inextensible layer can refer to an inextensible or a practically inextensible layer.

In some embodiments comprising two or more layers, the internal layer 132 can be slightly oversized compared to an inextensible outer second layer 133 such that the internal forces can be transferred to the high-strength inextensible outer second layer 133. One embodiment comprises a bellows 130 with an impermeable polyurethane polymer film inner first layer 132 and a woven nylon braid as the outer second layer 133.

The bellows 130 can be constructed in various suitable ways in further embodiments, which can include a single layer design that is constructed of a material that provides both fluid impermeability and that is sufficiently inextensible. Other examples can include a complex bellows assembly that comprises multiple laminated layers that are fixed together into a single structure. In some examples, it can be necessary to limit the deflated stack height of the bellows 130 to maximize the range of motion of the leg actuator unit 110. In such an example, it can be desirable to select a low-thickness fabric that meets the other performance needs of the bellows 130.

In yet another embodiment, it can be desirable to reduce friction between the various layers of the bellows 130. In one embodiment, this can include the integration of a third layer 134 that acts as an anti-abrasive and/or low friction intermediate layer between the first and second layers 132, 133. Other embodiments can reduce the friction between the first and second layers 132, 133 in alternative or additional ways, including but not limited to the use of a wet lubricant, a dry lubricant, or multiple layers of low friction material. Accordingly, while the example of FIG. 10*a* illustrates an example of a bellows 130 comprising three layers 132, 133, 134, further embodiments can include a bellows 130 having any suitable number of layers, including one, two, three, four, five, ten, fifteen, twenty five, and the like. Such one or more layers can be coupled together along adjoining faces in part or in whole, with some examples defining one or more cavities between layers. In such examples, material such as lubricants or other suitable fluids can be disposed in such cavities or such cavities can be effectively empty. Additionally, as described herein, one or more layers (e.g., the third layer 134) need not be a sheet or planar material layer as shown in some examples and can instead comprise a layer defined by a fluid. For example, in some embodiments, the third layer 134 can be defined by a wet lubricant, a dry lubricant, or the like.

The inflated shape of the bellows 130 can be important to the operation of the bellows 130 and/or leg actuator unit 110 in some embodiments. For example, the inflated shape of the bellows 130 can be affected through the design of both an impermeable and inextensible portion of the bellows 130 (e.g., the first and second layer 132, 133). In various embodiments, it can be desirable to construct one or more of the layers 132, 133, 134 of the bellows 130 out of various two-dimensional panels that may not be intuitive in a deflated configuration.

In some embodiments, one or more impermeable layers can be disposed within the bellows cavity 131 and/or the bellows 130 can comprise a material that is capable of holding a desired fluid (e.g., a fluid impermeable first internal layer 132 as discussed herein). The bellows 130 can comprise a flexible, elastic, or deformable material that is operable to expand and contract when the bellows 130 are inflated or deflated as described herein. In some embodiments, the bellows 130 can be biased toward a deflated configuration such that the bellows 130 is elastic and tends to return to the deflated configuration when not inflated. Additionally, although bellows 130 shown herein are configured to expand and/or extend when inflated with fluid, in some embodiments, bellows 130 can be configured to shorten and/or retract when inflated with fluid in some examples. Also, the term 'bellows' as used herein should not be construed to be limiting in any way. For example the term 'bellows' as used herein should not be construed to require elements such as convolutions or other such features (although convoluted bellows 130 can be present in some embodiments). As discussed herein, bellows 130 can take on various suitable shapes, sizes, proportions and the like.

In various embodiments, the bellows 130 can comprise a bellows and/or bellows system as described in related U.S. patent application Ser. No. 14/064,071 filed Oct. 25, 2013, which issued as U.S. Pat. No. 9,821,475; as described in U.S. patent application Ser. No. 14/064,072 filed Oct. 25, 2013; as described in U.S. patent application Ser. No. 15/823,523 filed Nov. 27, 2017; or as described in U.S. patent application Ser. No. 15/472,740 filed Mar. 29, 2017.

In some applications, the design of the fluidic actuator unit 110 can be adjusted to expand its capabilities. One example of such a modification can be made to tailor the torque profile of a rotary configuration of the fluidic actuator unit 110 such that the torque changes as a function of the angle of the joint structure 125. To accomplish this in some examples, the cross-section of the bellows 130 can be manipulated to enforce a desired torque profile of the overall fluidic actuator unit 110. In one embodiment, the diameter of the bellows 130 can be reduced at a longitudinal center of the bellows 130 to reduce the overall force capabilities at the full extension of the bellows 130. In yet another embodiment, the cross-sectional areas of the bellows 130 can be modified to induce a desired buckling behavior such that the bellows 130 does not get into an undesirable configuration. In an example embodiment, the end configurations of the bellows 130 of a rotary configuration can have the area of the ends reduced slightly from the nominal diameter to provide for the end portions of the bellows 130 to buckle under loading until the actuator unit 110 extends beyond a predetermined joint angle, at which point the smaller diameter end portion of the bellows 130 would begin to inflate.

In other embodiments, this same capability can be developed by modifying the behavior of the constraining ribs 135. As an example embodiment, using the same example bellows 130 as discussed in the previous embodiment, two constraining ribs 135 can fixed to such bellows 130 at evenly distributed locations along the length of the bellows 130. In some examples, a goal of resisting a partially inflated buckling can be combated by allowing the bellows 130 to close in a controlled manner as the actuator unit 110 closes. The constraining ribs 135 can be allowed to get closer to the joint structure 125 but not closer to each other until they have bottomed out against the joint structure 125. This can allow the center portion of the bellows 130 to remain in a fully inflated state which can be the strongest configuration of the bellows 130 in some examples.

In further embodiments, it can be desirable to optimize the fiber angle of the individual braid or weave of the bellows 130 in order to tailor specific performance characteristics of the bellows 130 (e.g., in an example where a bellows 130 includes inextensibility provided by a braided or woven fabric). In other embodiments, the geometry of the bellows 130 of the actuator unit 110 can be manipulated to allow the robotic exoskeleton system 100 to operate with different characteristics. Example methods for such modification can include but are not limited to the following: the use of smart materials on the bellows 130 to manipulate the mechanical behavior of the bellows 130 on command; or the mechanical modification of the geometry of the bellows 130 through means such as shortening the operating length and/or reducing the cross sectional area of the bellows 130.

Figure 12:
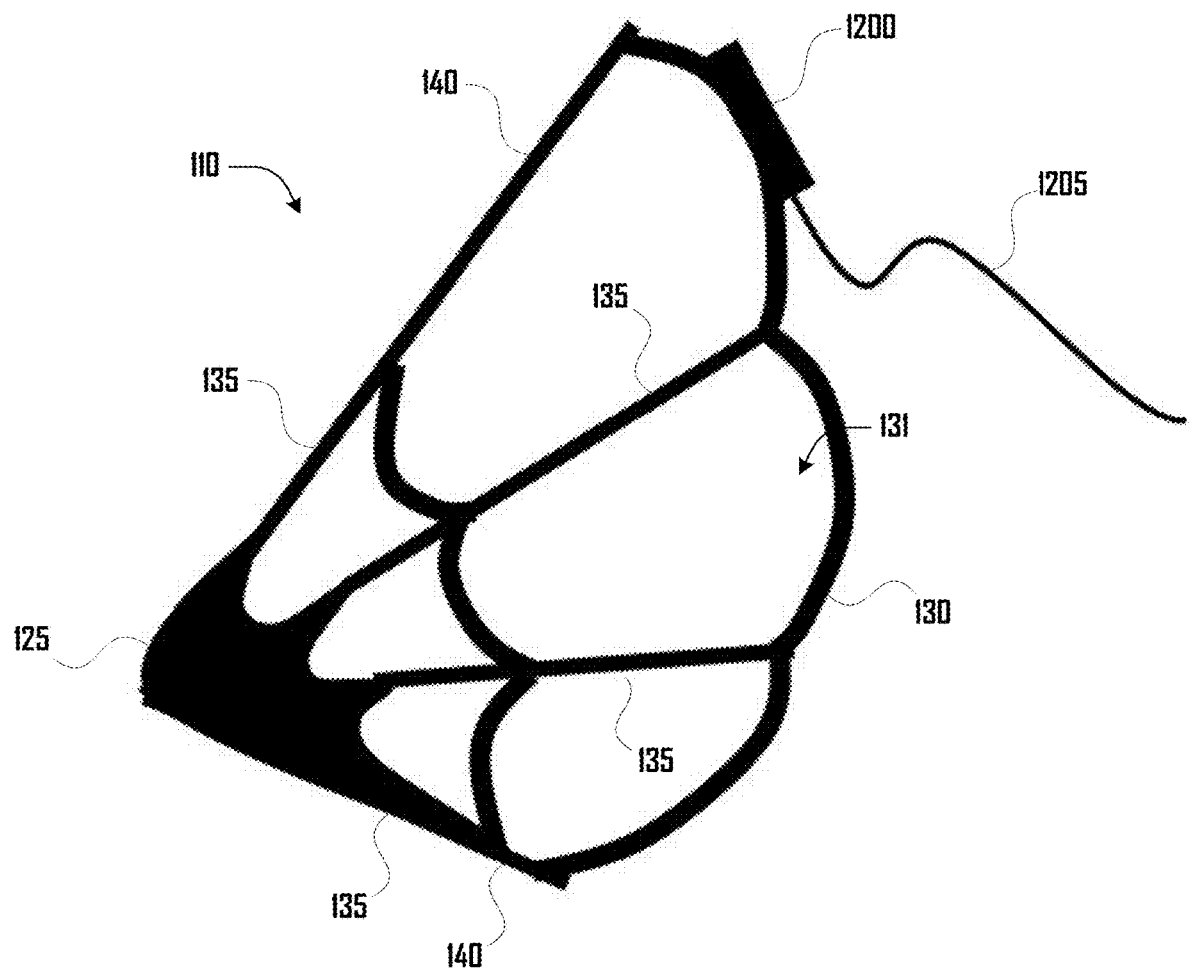

An example embodiment of this includes a bellows 130 having an inextensible layer with embedded shape memory alloy segments, such that when the embedded shape memory alloy segments are exposed to an electrical impulse, the stiffness of the embedded shape memory alloy segments change, causing the bellows 130 to perform differently when placed under pressure or in other conditions. For example, FIG. 12 illustrates an example of an actuation unit 110 having bellows 130 with an electrical impulse unit 1200 coupled to the bellows 130, which can provide an electrical impulse or other electrical signal to the bellows 130 via a line 1205, which in some examples can be operably coupled to the exoskeleton device 510 (see FIG. 5). Accordingly, in some embodiments the exoskeleton device 510 can control the stiffness, shape, or other suitable configuration of one or more bellows 130 of one or more actuator units 110 via the electrical impulse unit 1200. Such control can be based on data received from sensors 513 of the exoskeleton device 510, which can include data indicating an activity being performed by a user 101 (e.g., walking, standing, running, jumping, squatting, ascending stairs, descending stairs, landing, turning, sitting, grasping, skiing, reaching, and the like); a state of one or more portions of the actuation unit 110 (e.g., arms 115, 120, joint 125, bellows 130, ribs 135, or the like); environmental condition data; and the like. In other words, the configuration of one or more bellows 130 can be selectively configured in real time by the exoskeleton device 510 based on various states that can be determined by the exoskeleton device 510 based on data obtained by the exoskeleton device 510.

In further examples, a fluidic actuator unit 110 can comprise a single bellows 130 or a combination of multiple bellows 130, each with its own composition, structure, and geometry. For example, some embodiments can include multiple bellows 130 disposed in parallel or concentrically on the same joint assembly 125 that can be engaged as needed. In one example embodiment, a joint assembly 125 can be configured to have two bellows 130 disposed in parallel directly next to each other. The system 100 can selectively choose to engage each bellows 130 as needed to allow for various amounts of force to be output by the same fluidic actuator unit 110 in a desirable mechanical configuration.

In further embodiments, a fluidic actuator unit 110 can include various suitable sensors to measure mechanical properties of the bellows 130 or other portions of the fluidic actuator unit 110 that can be used to directly or indirectly estimate pressure, force, or strain in the bellows 130 or other portions of the fluidic actuator unit 110. In some examples, sensors located at the fluidic actuator unit 110 can be desirable due to the difficulty in some embodiments associated with the integration of certain sensors into a desirable mechanical configuration while others may be more suitable. Such sensors at the fluidic actuator unit 110 can be operably connected to the exoskeleton device 510 (see FIG. 5) and the exoskeleton device 510 can use data from such sensors at the fluidic actuator unit 110 to control the exoskeleton system 100.

The described embodiments are susceptible to various modifications and alternative forms, and specific examples thereof have been shown by way of example in the drawings and are herein described in detail. It should be understood, however, that the described embodiments are not to be limited to the particular forms or methods disclosed, but to the contrary, the present disclosure is to cover all modifications, equivalents, and alternatives.

What is claimed is:

1. A wearable pneumatic exoskeleton system that comprises:
   a left and right pneumatic leg actuator unit configured to be respectively associated with a left and right leg of a user wearing the pneumatic exoskeleton system, the left and right pneumatic actuator units each including:
      a rotatable joint disposed laterally and adjacent to a respective knee of the user with a rotational joint axis of the rotatable joint being disposed coincident with a rotational axis of the respective knee of the user wearing the pneumatic exoskeleton system,
      an upper arm coupled to the rotatable joint and extending along a length of an upper leg portion above the knee of the user wearing the pneumatic exoskeleton system,
      a lower arm coupled to the rotatable joint and extending along a length of a lower leg portion below the knee of the user wearing the pneumatic exoskeleton system, with a distal end of the lower arm coupled to a ski boot of a skiing assembly that includes a pair of ski boots and skis,
      a first and second plate extending from the rotatable joint,
      an inflatable bellows actuator extending between the first and second plate and defining a bellows cavity, the inflatable bellows actuator configured to extend along a length of the bellows actuator when pneumatically inflated by introducing pneumatic fluid into the bellows cavity, and
      a plurality of constraint ribs extending from the rotatable joint and encircling portions of the bellows actuator along the length of the bellows actuator;
   a pneumatic system configured to introduce pneumatic fluid to the bellows actuators of the pneumatic leg actuator units to independently actuate the bellows actuators, and
   an exoskeleton computing device including:
      a plurality of sensors,
      a memory storing at least a control program, and
      a processor that executes the control program to control the pneumatic system based at least in part on data obtained by the exoskeleton computing device including sensor data obtained from the plurality of sensors.

2. The wearable pneumatic exoskeleton system of claim 1, wherein the bellows actuators each further comprise:
   an internal first layer that defines the bellows cavity, the internal first layer being substantially impermeable to the pneumatic fluid; and
   an outer second layer comprising an inextensible planar material that is substantially inextensible along the plane axes of the planar material while being flexible in other directions.

3. The wearable pneumatic exoskeleton system of claim 2, wherein the bellows actuators each further comprise a third layer disposed between the first and second layers that acts as an anti-abrasive and/or low-friction intermediate layer between the first and second layers.

4. The wearable pneumatic exoskeleton system of claim 1, wherein each of the bellows actuators further include:
   one or more embedded shape memory alloy segments that change stiffness in response to an electrical impulse, and
   an electrical impulse unit coupled to the bellows actuators that provides an electrical impulse to the respective embedded shape memory alloy segments to change the stiffness of the respective bellows actuators, the electrical impulse unit operably coupled to the exoskeleton computing device such that the exoskeleton computing device can selectively control the stiffness of the respective bellows actuators.

5. The wearable pneumatic exoskeleton system of claim 1, wherein the constraint ribs comprise a pair of rib arms that extend from the rotatable joint and couple with a circular rib ring that defines a rib cavity through which a portion of the respective bellows actuators extend.

6. A wearable exoskeleton system that comprises:
   a leg actuator unit configured to be worn on a leg of a user wearing the exoskeleton system, the leg actuator unit including:
      a joint aligned with a knee of the user wearing the exoskeleton system;
      an upper arm coupled to the joint and extending along a length of an upper leg portion above the knee of the user wearing the exoskeleton system;
      a lower arm coupled to the joint and extending along a length of a lower leg portion below the knee of the user wearing the exoskeleton system, with a distal end of the lower arm coupled to a ski boot of a skiing assembly including the ski boot and a ski;
      a first and second plate extending from the joint;
      an inflatable bellows actuator extending between the first and second plate and defining a bellows cavity, the inflatable bellows actuator configured to extend along a length of the bellows actuator when inflated by introducing fluid into the bellows cavity; and
      one or more constraint ribs extending from the joint and surrounding portions of the bellows actuator along the length of the bellows actuator.

7. The wearable pneumatic exoskeleton system of claim 6, wherein the bellows actuator further comprises:
   an internal first layer that defines the bellows cavity, the internal first layer being substantially impermeable to the fluid used to inflate the bellows actuator;
   an outer second layer comprising an inextensible planar material that is substantially inextensible along one or more plane axes of the planar material while being flexible in other directions; and
   a third layer disposed between the first and second layers that acts as an anti-abrasive and/or low friction intermediate layer between the first and second layers.

8. A fluidic actuator unit comprising:
   a joint configured to be aligned with a knee of a user when the user is wearing the fluidic actuator unit;
   a first arm coupled to the joint;
   a second arm coupled to the joint, with a distal end of the second arm coupled to a ski boot of a skiing assembly including one or more skis;
   an inflatable bellows actuator extending between a first and second plate associated with the joint, the inflatable bellows actuator defining a bellows cavity, the inflatable bellows actuator configured to extend along a length of the bellows actuator when inflated by introducing fluid into the bellows cavity; and
   one or more constraint ribs extending from the joint and surrounding portions of the bellows actuator along the length of the bellows actuator.

9. The fluidic actuator unit of claim 8, wherein the fluidic actuator unit is disposed lateral to the knee of the user when the user is wearing the fluidic actuator.

10. The fluidic actuator unit of claim 9, wherein the joint is aligned with the knee of the user about a common rotational axis when the user is wearing the fluidic actuator unit.

11. The fluidic actuator unit of claim 9, wherein the first arm is configured to extend along a length of an upper leg portion above the knee of the user wearing fluidic actuator unit; and wherein the second arm is configured to extend along a length of a lower leg portion below the knee of the user wearing the fluidic actuator unit.

12. The fluidic actuator unit of claim 8, wherein the first and second plates extend from the joint.

13. The fluidic actuator unit of claim 8, wherein the bellows actuator comprises a layer that defines the bellows cavity, the layer being substantially impermeable to a fluid used to inflate the bellows.

14. The fluidic actuator unit of claim 8, wherein the bellows actuator comprises a layer comprising an inextensible planar material that is substantially inextensible along one or more plane axes of the planar material while being flexible in other directions.

15. The fluidic actuator unit of claim 8, wherein the bellows actuator comprises a third layer disposed between a first and second layer of the bellows, the third layer being an anti-abrasive and/or low friction intermediate layer between the first and second layers.

16. The fluidic actuator unit of claim 8, wherein the one or more constraint ribs comprise one or more rib arms that extend from the joint and couple with a rib ring that defines a rib cavity through which a portion of the bellows actuator extends.

\* \* \* \* \*